United States Patent
Fogg et al.

(10) Patent No.: US 11,253,285 B2
(45) Date of Patent: Feb. 22, 2022

(54) SUBCUTANEOUS CUTTING DEVICE

(71) Applicant: UNIVERSITY OF UTAH RESEARCH FOUNDATION, Salt Lake City, UT (US)

(72) Inventors: Benjamin Fogg, Salt Lake City, UT (US); Blake Corcoran, Salt Lake City, UT (US); Kellen Arlen Hilton, Salt Lake City, UT (US); Daniel Cushman, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 147 days.

(21) Appl. No.: 16/089,359

(22) PCT Filed: Apr. 4, 2017

(86) PCT No.: PCT/US2017/026004
§ 371 (c)(1),
(2) Date: Sep. 27, 2018

(87) PCT Pub. No.: WO2017/176800
PCT Pub. Date: Oct. 12, 2017

(65) Prior Publication Data
US 2020/0305918 A1    Oct. 1, 2020

Related U.S. Application Data

(60) Provisional application No. 62/317,959, filed on Apr. 4, 2016.

(51) Int. Cl.
*A61B 17/32*       (2006.01)
*A61B 17/3211*     (2006.01)
*A61B 17/34*       (2006.01)

(52) U.S. Cl.
CPC .............. *A61B 17/320036* (2013.01); *A61B 17/32002* (2013.01); *A61B 17/3211* (2013.01);
(Continued)

(58) Field of Classification Search
CPC .. A61B 2017/32113; A61B 17/320036; A61B 17/3211; A61B 17/32002
See application file for complete search history.

(56) References Cited

U.S. PATENT DOCUMENTS 2,668,537 A * 2/1954 Kapp ................. A61B 17/3201
606/174
4,962,770 A   10/1990 Agee et al.
(Continued)

OTHER PUBLICATIONS

International Search Report and Written Opinion, United States International Search Authority, dated Jul. 6, 2017, PCT/US2017/026004.
(Continued)

*Primary Examiner* — Sarah A Simpson
(74) *Attorney, Agent, or Firm* — Workman Nydegger (57) ABSTRACT

The present disclosure describes a subcutaneous cutting device for insertion into tissues and cutting of targeted tissues. The cutting device includes a handle, a cannula extending distally from the handle to a sharpened distal tip, and an adjustable blade disposed within a blade-holding section of the cannula. The blade is selectively adjustable between a retracted position within the cannula and an open position with the blade tip lifted up and angled away from the cannula. When the blade is in the open position, the blade tip points proximally toward the handle.

20 Claims, 6 Drawing Sheets

(52) U.S. Cl.
CPC . *A61B 17/3403* (2013.01); *A61B 2017/32113* (2013.01); *A61B 2017/3413* (2013.01)

(56) References Cited

U.S. PATENT DOCUMENTS

| | | | |
|---|---|---|---|
| 5,089,000 A | | 2/1992 | Agee et al. |
| 5,569,283 A | | 10/1996 | Green et al. |
| 5,586,990 A | * | 12/1996 | Hahnen .......... A61B 17/320016 |
| | | | 606/167 |
| 6,602,267 B2 | | 8/2003 | Castaneda |
| 6,685,717 B1 | | 2/2004 | Ilic |
| 8,579,930 B2 | | 11/2013 | Palmer et al. |
| 8,603,124 B1 | | 12/2013 | Hatch |
| 8,652,157 B2 | | 2/2014 | McCormack et al. |
| 8,771,303 B1 | | 7/2014 | Jurbala |
| 9,730,721 B2 | | 8/2017 | Gill et al. |
| 9,993,259 B2 | | 6/2018 | Barnes et al. |
| 2006/0190021 A1 | | 8/2006 | Hausman et al. |
| 2007/0288043 A1 | | 12/2007 | Rehnke |
| 2008/0109021 A1 | | 5/2008 | Medoff |
| 2011/0118601 A1 | | 5/2011 | Barnes et al. |
| 2012/0165725 A1 | * | 6/2012 | Chomas .............. A61M 1/0039 |
| | | | 604/22 |
| 2014/0121456 A1 | | 5/2014 | McCormack et al. |
| 2016/0081710 A1 | | 3/2016 | Barnes et al. |

OTHER PUBLICATIONS

International Search Report and Written Opinion for PCT/US2017/026004 dated Jul. 6, 2017.

* cited by examiner

SUBCUTANEOUS CUTTING DEVICE

CROSS-REFERENCE TO RELATED APPLICATIONS

This application claims priority to PCT Application No. PCT/US2017/026004, filed Apr. 4, 2017, entitled "SUBCUTANOUS CUTTING DEVICE", which claims the benefit of and priority to U.S. Provisional Application No. 62/317,959, filed Apr. 4, 2016 entitled "SUBCUTANEOUS CUTTING DEVICE". All the aforementioned applications are incorporated by reference herein in their entirety.

BACKGROUND

Certain medical procedures require the cutting of a patient's subcutaneous tissues. For example, carpal tunnel release, tarsal tunnel release, plantar fascia release, and lateral retinacular release of the knee require the cutting of subcutaneous tissue. In many such procedures, swelling or malformation of tissues leads to impinging of anatomically nearby nerves, causing pain. Other conditions may not necessarily impinge on nerves, but can include swollen or malformed tissues which disrupt proper functioning of other nearby anatomical structures. Cutting the swollen or malformed tissue can provide more space for the impinged nerves or can otherwise lessen the disruption to nearby anatomy.

However, in order to cut the targeted tissue at the root of the condition, a cutting device must be delivered to the targeted tissue, the targeted tissue must be appropriately cut, and the cutting device must be removed from the patient. Such procedures carry risks of accidental injury to non-targeted tissues. In addition, many such procedures are done under general anesthesia, which itself carries risks and precludes some patients from undergoing treatment. While minimally-invasive procedures can avoid the need for general anesthesia, typical methods require large entry incisions and/or multiple entry incisions, which can increase the risk of tissue damage and infection.

Further, cutting the targeted tissue must often be done in relatively crowded anatomical spaces. Injury of surrounding, non-targeted tissues must be avoided during delivery of the device and during cutting of the targeted tissue. Once the targeted tissue has been sufficiently cut, the device must be removed from the patient while minimizing cutting or injury of the non-targeted tissues. These technical challenges can make it difficult to increase the safety and effectiveness of such subcutaneous tissue cutting procedures.

BRIEF SUMMARY

The present disclosure describes embodiments of medical devices configured for cutting subcutaneous tissues. In some embodiments, a medical device includes a handle and a cannula coupled to the handle and extending distally from the handle. The cannula includes a distal tip and a blade-holding section near the distal tip. A blade is disposed within the blade-holding section of the cannula. The blade is adjustable between a retracted position in which the blade is disposed within the blade-holding section of the cannula and an open position in which the blade tip is rotated away from the cannula. In preferred embodiments, the blade tip is angled toward the handle in a "reverse cutting" orientation when in the open position. A control mechanism operatively couples the handle to the blade to enable selective adjustment of the blade between the retracted and open positions.

In some embodiments, the blade is pivotally coupled to the cannula by a connection member (e.g., pin, shaft, axle) disposed near the blade heel. The connection member enables the blade tip to be rotated away from the cannula when moved toward the open position. In some embodiments, the distal tip of the cannula is sharpened so that the distal tip may be used to puncture dermal tissue or other overlying tissues for delivery of the cannula to the targeted treatment site.

In use, a physician or other device operator may grip the handle and direct the cannula to a targeted treatment site within a patient's tissues. The distal tip can be used to puncture dermal tissues and any other overlying tissues to enable delivery of the distal section of the cannula to the treatment site. During the initial delivery of the cannula through the patient's tissue, the blade may be maintained in the retracted configuration.

The cannula may be positioned so that the blade-holding section is positioned near the targeted cutting site (e.g., a short distance distally beyond the targeted cutting site). Once the device is properly positioned, the operator may manipulate the controller to move the blade from the retracted position to the open position, thereby exposing the cutting edge of the blade. The operator may then move the device to bring the blade into contact with targeted tissues. In some implementations, cutting of the targeted tissue may be achieved by simply reversing the cannula a distance through the tissue tract created during initial delivery of the cannula to the target. After the targeted tissue has been sufficiently cut, the blade may then be moved back to the retracted position, and the cannula fully reversed and removed from the patient.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe various features and concepts of the present disclosure, a more particular description of certain subject matter will be rendered by reference to specific embodiments which are illustrated in the appended drawings. Understanding that these figures depict just some example embodiments and are not to be considered to be limiting in scope, various embodiments will be described and explained with additional specificity and detail through the use of the accompanying drawings in which.

DETAILED DESCRIPTION

The present disclosure describes embodiments of a subcutaneous cutting device which may be utilized to cut nerve, muscle, tendon, vessels, ligament, or other targeted tissue. Some embodiments described herein may be utilized to cut targeted tissue in order to relieve pressure and provide therapeutic pressure release to nearby anatomical tissues and/or structures. In certain implementations, a subcutaneous cutting device as described herein may be utilized, for example, for carpal tunnel release, tarsal tunnel release, plantar fascia release, trigger finger/thumb release, lateral retinacular release of the knee, other fascial release (e.g., compartment syndrome etc.), peripheral nerve release (e.g., sciatic nerve, cubital tunnel release, etc.), cyst puncture and/or incision (e.g., Baker's cyst, ganglion cyst, etc.), muscle release (e.g., spasticity treatment, accessory muscle removal, etc.) and tenotomy (e.g., microincision of a tendon to promote healing).

Figure 1:
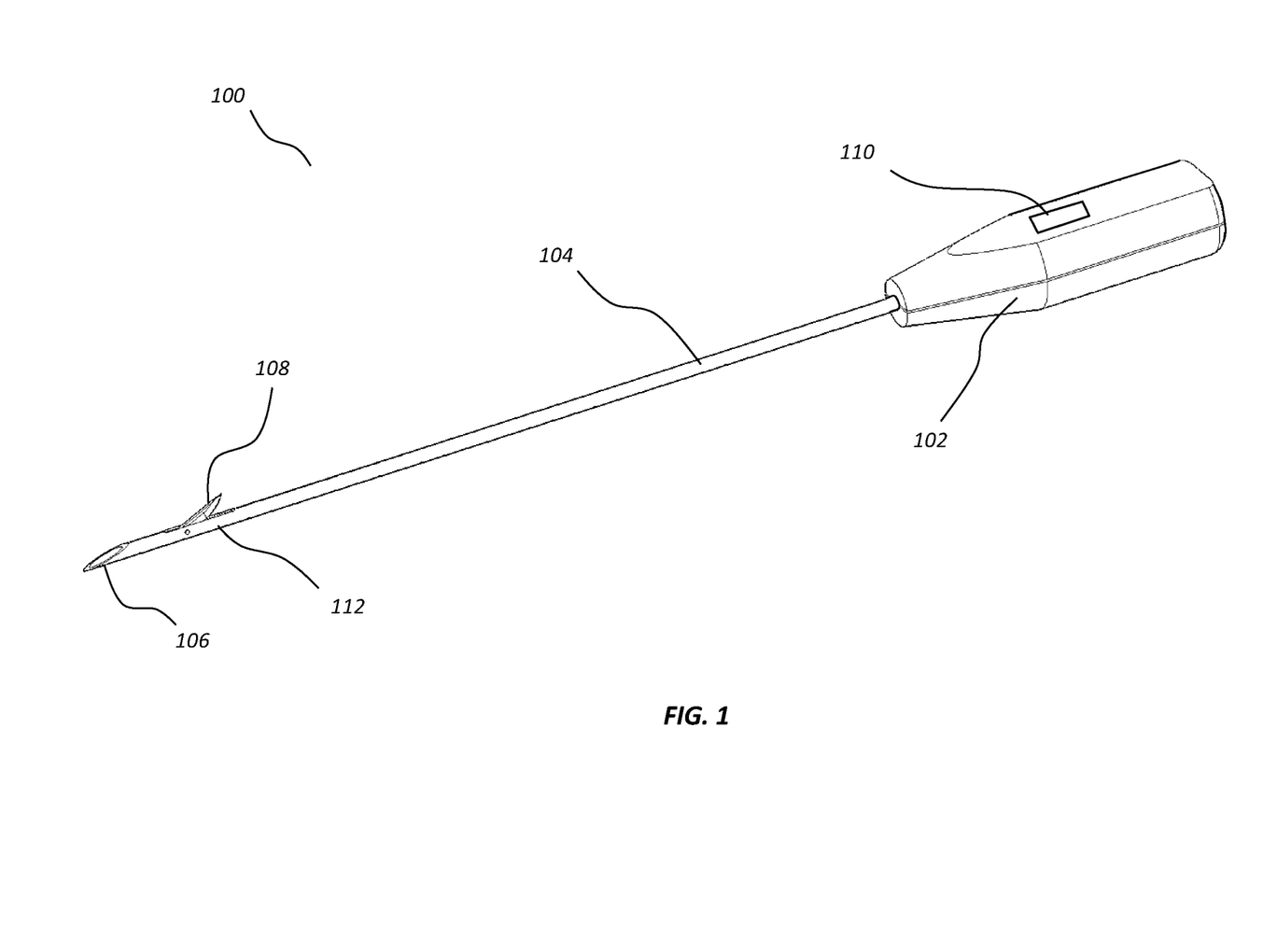
FIG. 1 is a perspective view of an exemplary subcutaneous cutting device.

FIG. 1 illustrates an exemplary embodiment of a subcutaneous cutting device 100. As shown, the illustrated embodiment includes a proximal handle 102 and a cannula 104 coupled to the handle 102 and extending distally from the handle 102. The cannula 104 includes a distal tip 106. In preferred embodiments, the distal tip 106 is sharpened (e.g., angle cut, ground, and/or otherwise tapered to a smaller diameter relative to immediately proximal regions) to enable puncturing of overlying tissues for delivery of the distal tip 106 to a targeted treatment area. For example, the distal tip 106 may be beveled (as shown), conical-shaped, or pencil-point-shaped.

The cannula 104 may be configured as a surgical needle, tip-sharpened hypotube, or other suitable structure capable of delivery to a targeted treatment area. The length of the cannula 104 may be varied according to particular application needs (e.g., according to depth of targeted tissue). In some embodiments, the cannula 104 has a length of about 5 to 20 cm, or about 8 to 15 cm. The outer diameter of the cannula 104 may also be varied. In general, the smallest diameter able to provide sufficient structural integrity during use is preferred. In some embodiment, the cannula 104 has an outer diameter of about 0.5 to 2 mm (e.g., a needle having a gauge of about 24 to 14). In some embodiments, the cannula 104 is detachable from the handle 102. For example, the handle 102 may be reusable, while the cannula 104 and blade 108 are disposable.

The subcutaneous cutting device 100 also includes an adjustable blade 108 disposed at a blade-holding section 112 of the cannula 104, which is disposed near the distal tip 106 of the device (e.g., about 0.25 to 5 cm, or about 0.5 to 2 cm away from the distal tip 106). As explained in more detail below, the blade 108 is configured to be selectively moved between a retracted position and an open position. The blade 108 is shown in FIG. 1 in the open position. In the retracted position, the blade 108 is positioned within the cannula 104 so that no portion of the blade 108 extends beyond the outer surface of the cannula 104. In the open position, the blade 108 is angled so that the blade tip is rotated away from the longitudinal axis of the cannula 104. Although a single blade is shown in the illustrated embodiments, it will be understood that other embodiments may include multiple blades. For example, additional blades may be disposed at different sections along the axis of the cannula 104 and/or may be disposed at different circumferential positions around the circumference of the cannula 104.

The blade 108 is operatively connected to a controller 110 disposed on the handle 102. The controller 110 enables an operator to selectively adjust the blade 108 between the open and retracted positions through manual adjustment of the controller 110. The controller 110 may be configured as one or more buttons, sliders, track wheels, switches, dials, knobs, levers, solenoid actuator, other manually manipulatable objects, or combinations thereof. The handle 102 preferably includes markings or other indicators or mechanisms to clearly identify when the blade is actuated to an open position versus a retracted position. In some embodiments, the controller 110 is only disposed on the upper side of the device (i.e., the side toward which the blade opens) to avoid inadvertent deployment of the blade.

At least some cutting device embodiments described herein can beneficially enable precise and effective cutting of targeted tissue. For example, as compared to a saw-based cutting device, the illustrated blade-based devices may provide for effective cutting with a single pass of the blade, whereas a saw-based cutting device typically requires more complicated and more potentially tissue injuring back and forth movements to cut targeted tissue.

Further, a subcutaneous cutting device as described herein can beneficially enable subcutaneous tissue cutting procedures to be readily performed in a simple and straightforward manner. For example, at least some of the cutting device embodiments described herein may be readily utilized without first requiring a separate puncture or incision step carried out using a separate device. In addition, at least some of the cutting device embodiments described herein may be readily utilized without requiring looping and guidance of the device through an initially placed guide rod or guide wire.

Figure 2:
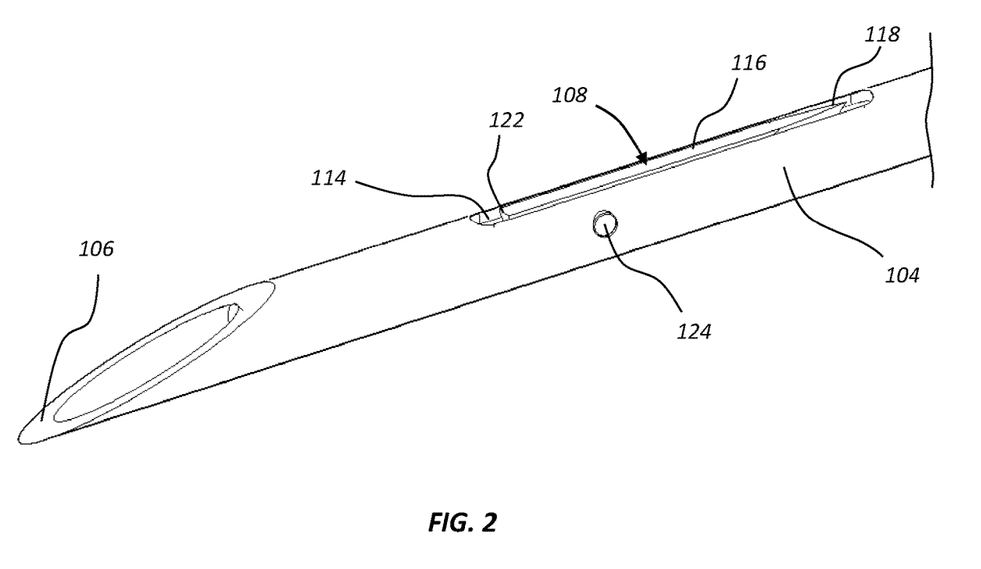
FIGS. 2 and 3 illustrate expanded views of the distal section of the subcutaneous cutting device of FIG. 1, showing the blade in a retracted and open state, respectively.
Figure 3:
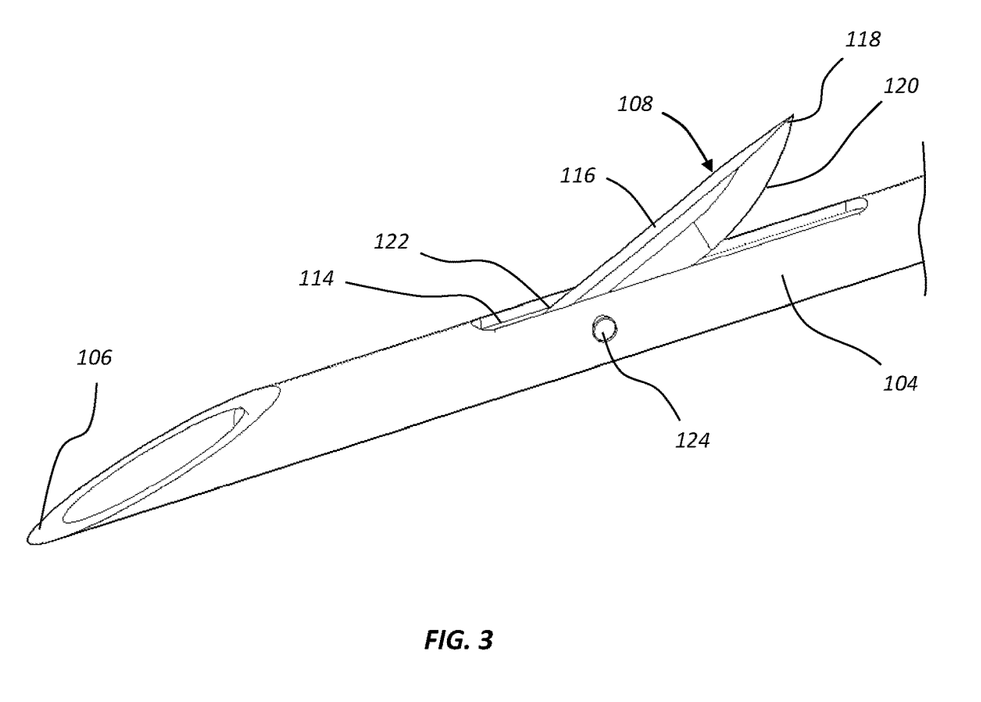

FIGS. 2 and 3 illustrate the distal tip 106 and blade 108 in expanded view. FIG. 2 illustrates the device with the blade 108 in the retracted position, and FIG. 3 illustrates the device with the blade 108 in the open position. In the illustrated embodiment, the distal tip 106 is shown as having an open, needle-like lumen. In alternative embodiments, at least a portion of the cannula 104 may have a solid-bore construction, including a closed tip. The cannula 104 can therefore have a hollow-bore construction, solid-bore construction, or combination with one or more sections being hollow and one or more being solid. The illustrated blade 108 includes a blade spine 116, blade tip 118, cutting edge 120, and blade heel 122.

The illustrated cannula 104 includes a blade slot 114 disposed along the longitudinal axis of the cannula 104. The slot 114 is configured to provide passage of the blade tip 118 out of and into the cannula 104 when moved between the retracted and open positions. The blade slot 114 may also beneficially provide for the passage of medicaments (e.g., anesthetic agent) through a lumen of the cannula 104 to the targeted treatment site. As shown, the distal-most extension of the distal tip 106 is disposed opposite the blade slot 114 (i.e., the bevel faces generally up toward the side of the blade slot 114). In other embodiments, the distal-most extension may be alternatively positioned. For example, the distal-most extension may be positioned on the same side as the blade slot 114 (i.e., so that the bevel faces opposite the blade slot side).

As shown in FIG. 2, when the blade 108 is in the retracted position, the blade spine 116 is positioned to be substantially flush with the outer surface of the cannula 104. This configuration beneficially minimizes the risk of the blade 108 inadvertently catching and/or injuring tissues as the cannula 104 is inserted into and removed from the patient. At the same time, the blade spine 116 substantially fills the blade slot 114 when the blade 108 is in the retracted position, which minimizes the break in continuity along the outer surface of the cannula 104 and prevents inadvertent catching of tissue within the blade slot 114.

The illustrated device includes a connection member 124 extending transversely (e.g., perpendicularly) through the length of the blade 108 to pivotally couple the blade 108 to the cannula 104. The connection member 124 may be configured as a pin (e.g., shaft, tube, axle, hinge, etc.), which functions as a pivot point for the blade 108 to rotate about when moving between the open and retracted positions. The connection member 124 is preferably disposed through a section of the blade near the blade heel 122 so as to position the pivot point opposite the blade tip 118 and thereby maximize the radius of rotation of the blade tip 118. For example, for a particular length of the blade 108, the connection member 124 is preferably disposed at the distal half, distal third, distal quarter, or distal eighth of the blade 108 (where distal refers to the direction toward the blade heel 122).

As shown in FIG. 3, when the blade 108 is moved to the open position, the blade 108 is rotated about the connection member 124 so that the blade tip 118 is rotated up and away from the cannula 104. This pivoting movement exposes the blade cutting edge 120 and positions the blade 108 at an angle with respect to the longitudinal axis of the cannula 104. As shown, the blade 108 is oriented so that the blade cutting edge 120 is disposed between the blade spine 116 and the cannula 104 and faces "downward" toward the cannula 104. This preferred orientation beneficially forms a cutting zone between the blade cutting edge 120 and the cannula 104. As shown, the cutting zone provides progressively less space between the blade cutting edge 120 and the cannula 104 along the distal direction. Alternative embodiments may utilize a double-sided blade, such as a blade having a second "upward" facing cutting edge in place of the blade spine. In some embodiments, one or more of the edges at the blade slot 114 may be sharpened to provide scissor-like functionality to the device. For example, the blade 108 may be repeatedly opened and closed to cut targeted tissue between the cutting edge of the blade and the sharpened edge(s) of the blade slot 114.

In the illustrated embodiment, the tip of the blade 108, when the blade 108 is in the open position, is angled toward the handle 102 and is thereby configured to provide for "reverse" cutting of the targeted tissue. For example, prior to opening the blade 108, the cannula 104 may be positioned so that the blade-holding section 112 is disposed just underneath and just distally beyond the targeted tissue to be cut. From this position, after the blade 108 is opened, cutting of the targeted tissue may be achieved by simply reversing the cannula 104 a distance through the tissue tract created during initial delivery of the cannula 104 to the target. After the targeted tissue has been sufficiently cut, the blade 108 may then be moved back to the retracted position, and the cannula 104 fully reversed and removed from the patient.

In use, a physician or other device operator may grip the handle 102 and direct the cannula 104 to a targeted treatment site within a patient's tissues. The distal tip 106 can be used to puncture dermal tissues and any other overlying tissues to enable delivery of the distal section of the cannula 104 to the treatment site. During the initial delivery of the cannula 104 through the patient's tissue, the blade 108 is maintained in the retracted configuration.

The cannula 104 may be positioned so that the blade-holding section 112 is positioned near the targeted cutting site (e.g., a short distance distally beyond the targeted cutting site). Once the device 100 is properly positioned, the operator may manipulate the controller 110 to move the blade 108 from the retracted position to the open position, thereby exposing the blade 108. The operator may then move the device 100 to bring the blade 108 into contact with targeted tissues.

In use, the reverse-oriented blade 108 can function to effectively "grab" targeted tissue as the cannula 104 is reversed away from the punctured tissues. As the cannula 104 is moved further proximally, the tissue captured within the cutting zone between the cannula 104 and the cutting edge 120 will be forced further distally into the cutting zone. The captured tissue is compressed within the progressively decreasing space between the blade cutting edge 120 and the cannula 104 until the tissue is cut by the blade cutting edge 120.

As best shown in FIGS. 2 and 3, the connection member 124 is disposed so as to be stationary relative to the cannula 104 as the blade 108 is adjusted between the open and retracted positions. For example, to move the blade 108 from the retracted position to the open position, the blade 108 is rotated about the connection member 124, and the connection member 124 itself is not required to be longitudinally translated, adjusted in height, or otherwise repositioned with respect to the cannula 104. This configuration provides for ready adjustment between open and retracted positions while also allowing for a stable and relatively wear-resistant connection of the blade 108 to the cannula 104. In contrast, a cutting device utilizing a complex deployment mechanism with non-stationary (relative to the cannula) blade pivot point will have a higher risk of inadvertent breakage at a pivot point and/or of unwanted blade detachment.

When the blade 108 is in the open position, the acute angle between the cannula 104 and the blade 108 is preferably within a range of about 10 degrees to about 45 degrees, or about 15 degrees to about 45 degrees, or about 20 degrees to 35 degrees. The device may also be configured such that the open blade forms an acute angle within a range with endpoints defined by any two of the foregoing values. Other embodiments may be configured to extend to greater than 45 degrees, depending on particular application needs and/or operator preferences. A blade position within the foregoing ranges can beneficially enable effective tissue capture and cutting. In contrast, for example, a typically less-preferred perpendicular blade position (where the blade is positioned at 90 degrees from the cannula) would not form an angled cutting zone or provide the same ability to "grab" targeted tissues and direct them further against the cutting edge of the blade.

Embodiments with reverse-oriented blades enable effective and accurate cutting of the targeted tissue. In contrast to a forward-oriented blade requiring forward "pushing" of the device to cut tissue, a reverse-oriented configuration is able to grab a retinaculum, fascia, pulley, or other segment of targeted tissue as the device is reversed through the already-formed tissue tract. In this manner, the direction of travel of the device is already substantially defined by the tissue tract, and the risk of inadvertently engaging with or cutting non-targeted tissues is reduced.

In addition, because the tissue tract has already been formed prior to deployment of the blade, the reverse motion of the device once the blade is deployed is relatively easier and better controlled. In contrast, a forward cutting configuration requires further distal pushing of the device while the blade is deployed in order to cut targeted tissue. Guiding such a device into more distal tissue areas while simultaneously cutting the targeted tissue can increase the relative difficulty in manipulating and/or properly controlling the device.

The description is primarily directed to preferred embodiments having such reverse-oriented blades. It will be understood, however, that other embodiments may be configured with a forward or perpendicularly oriented blade. For example, the foregoing embodiments may be modified to be forward-oriented by repositioning (horizontally flipping) the blade 108 and pin so that the blade tip is more distal than the connection member 124.

Figure 4:
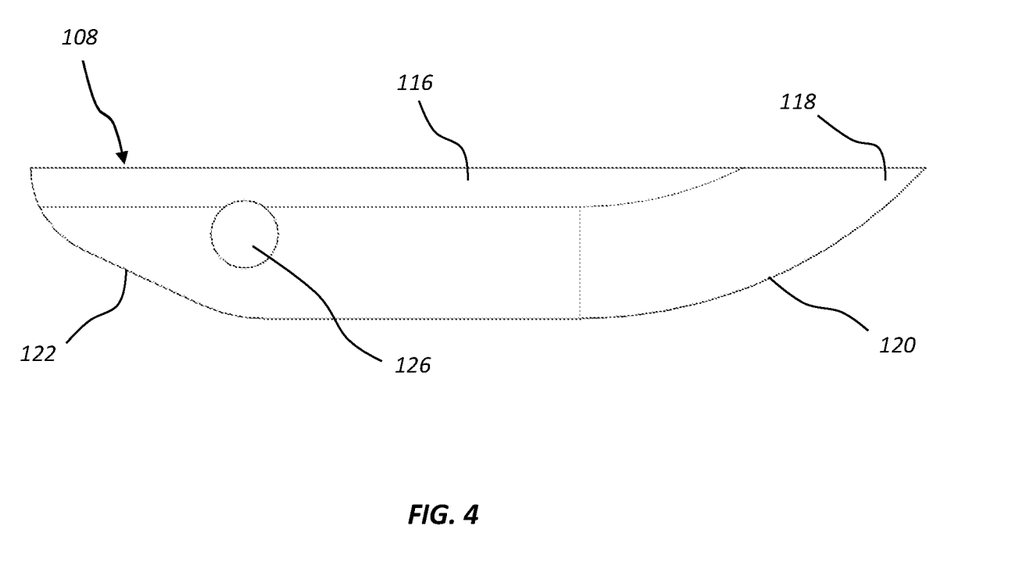
FIGS. 4 and 5 illustrate side and top views, respectively, of an exemplary blade which may be utilized in a subcutaneous cutting device.
Figure 5:
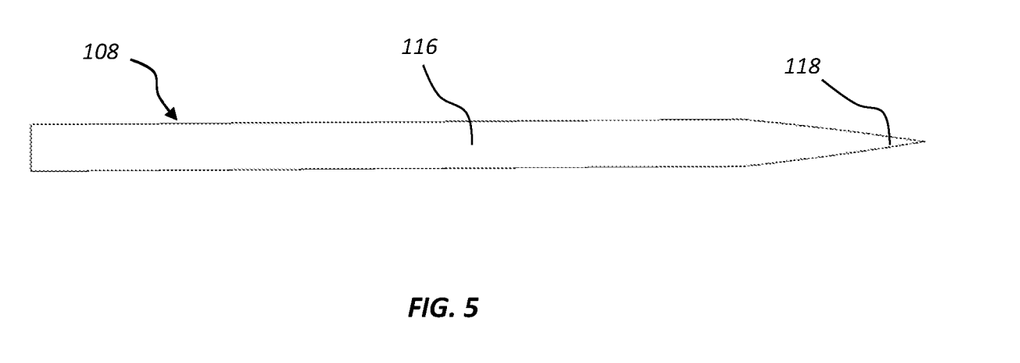

FIGS. 4 and 5 illustrate side and plan views, respectively, of the exemplary cutting blade 108, showing the blade spine 116, blade tip 118, blade cutting edge 120, and blade heel 122. As shown, the blade 108 also includes a connection hole 126 configured for engaging with the connection member 124, such as shown in FIGS. 2 and 3. The blade 108 may be sized according to particular application needs. In some embodiments, for example, the blade 108 may measure about 5 to 20 mm in length, and about 0.5 to 2.5 mm in height. Blade thickness may also vary according to particular application needs. In some embodiments, the blade thickness at the spine 116 is about 0.1 to 1 mm. The blade thickness tapers from the spine 116 toward the cutting edge 120 to a degree sufficient to perform effective cutting of targeted tissue.

The illustrated blade cutting edge 120 is configured as a smooth edge. In alternative embodiments, the blade cutting edge 120 may be serrated and/or may include one or more barbs, hooks, and/or forks (e.g., to provide a seam-ripper-like configuration).

In the illustrated embodiment, the blade heel 122 is configured as an angled backstop. As shown, the blade heel 122 and the blade cutting edge 120 may meet at a point substantially coinciding with the connection hole 126. The blade heel 122, configured in size and shape as an angled backstop, may provide stability to the blade 108 and may function to prevent over-rotation of the blade 108 when moved toward the open position. As explained in more detail below, the angle of the blade heel 122 can be set so as to define the maximum angle at which the blade 108 may be opened.

Figure 6:
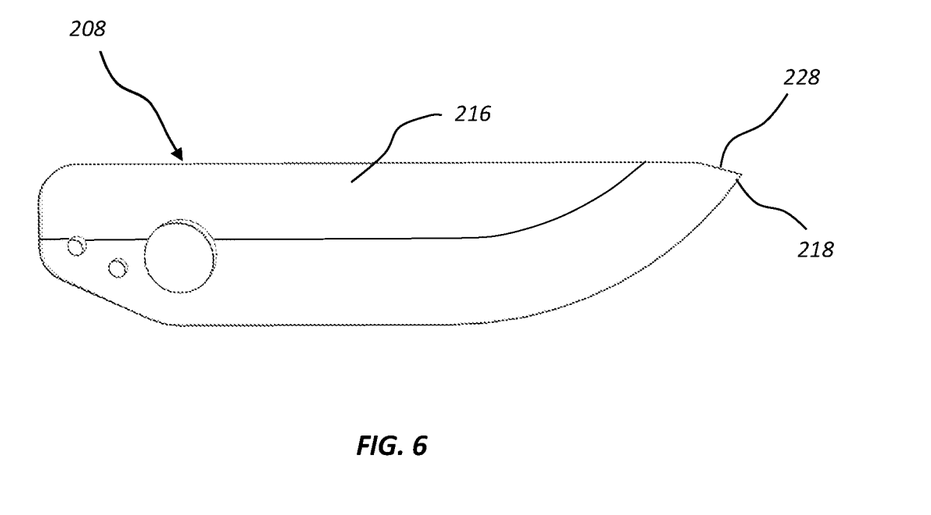
FIGS. 6 and 7 illustrate side and top views, respectively, of an alternative exemplary blade which may be utilized in a subcutaneous cutting device.
Figure 7:
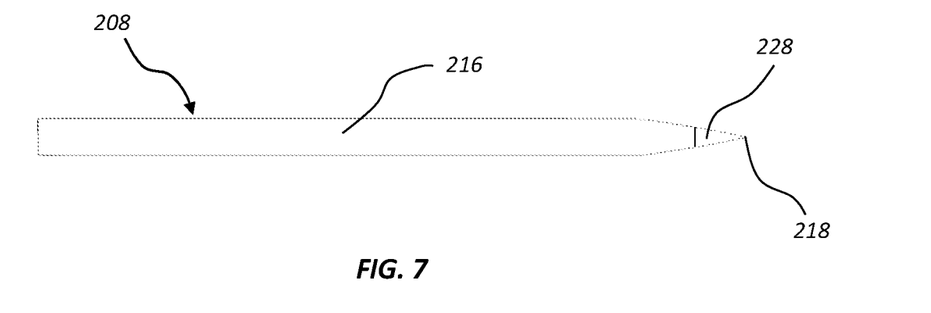

FIGS. 6 and 7 illustrate side and plan views, respectively of an alternative embodiment of a cutting blade 208 which may also be utilized with any of the subcutaneous cutting devices described herein. The illustrated blade 208 may be configured similarly to the blade 108 shown in FIGS. 4 and 5. As shown, the illustrated blade 208 also includes a tip notch 228. The tip notch 228 angles the blade tip 218 away from the blade spine 216. This structure causes the blade tip 218 to sit lower than the blade spine 216 within the cannula when the blade 208 is positioned within the cutting device and is in the retracted position. The tip notch 228 may thus function to prevent the blade tip 218 from inadvertently catching against tissue while the blade is retracted and the cutting device is being reversed. It will be understood that the foregoing blade descriptions are for exemplary blades only. Other blades having other shapes and/or features may also be utilized. For example some blade cutting edges may not be curved or may not be curved to the degree shown in the illustrated embodiments. Some blades may have differently oriented cutting edges, such as a double sided blade having upper and lower cutting edges.

Figure 8:
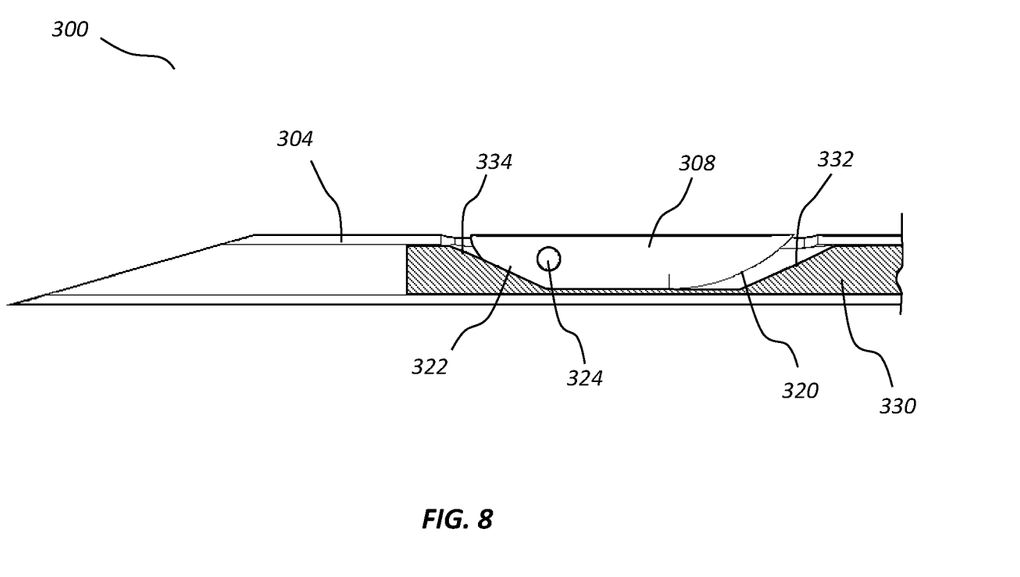
FIGS. 8 and 9 are cross-sectional views of a distal section of a subcutaneous cutting device showing a control mechanism for opening and retracting the blade.
Figure 9:
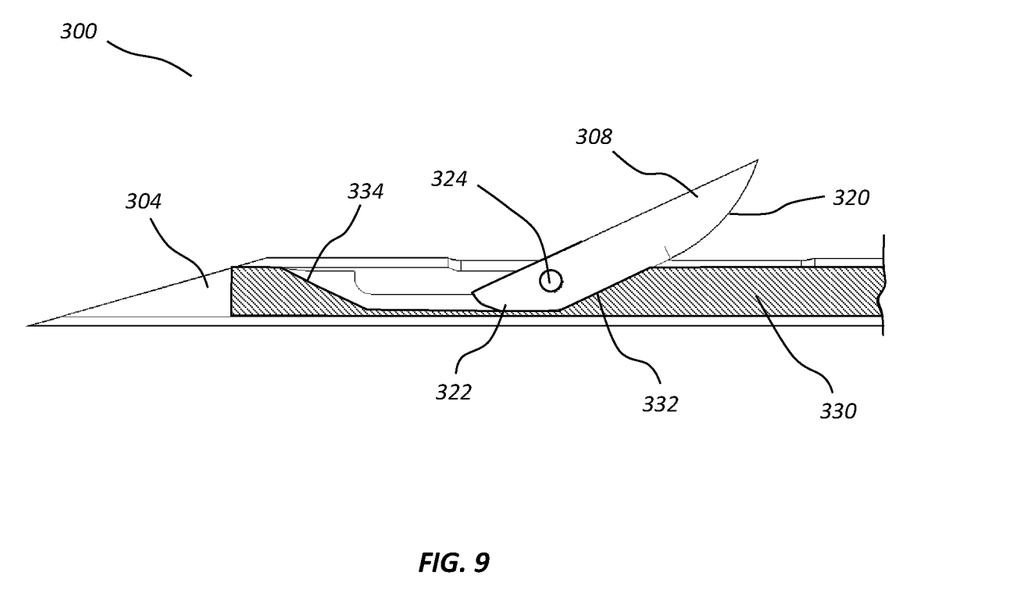

FIGS. 8 and 9 are cross-sectional views of an embodiment of a cutting device 300 showing an exemplary control mechanism that may be utilized to provide selective adjustment of a cutting blade 308 between the retracted and open positions. In the illustrated embodiment, the cutting device 300 includes a control rod 330 which is moveable within a lumen of the cannula 304. Although not shown in these views, the control rod 330 extends proximally to a handle of the device so that a device operator may selectively move the control rod 330 by manipulation of one or more controllers of the handle (see handle 102 and controller 110 of FIG. 1, for example).

As shown, the control rod 330 includes a proximal angled surface 332 and a distal angled surface 334. The angled surfaces 332 and 334 are configured to engage with the blade 308 to rotate the blade 308 between the open and retracted positions.

From the retracted blade position shown in FIG. 8, the control rod 330 may be translated distally within the lumen of the cannula 304. As the control rod 330 moves distally, the proximal angled surface 332 will be brought into contact with the blade cutting edge 320. Further distal movement of the control rod 330 will cause the blade 308 to lift and pivot about the connection member 324, thereby rotating the blade toward the open position shown in FIG. 9.

In the illustrated embodiment, the blade heel 322 is angled to form a backstop which prevents further rotation once the blade 308 has reached the full open position shown in FIG. 9. Additionally, or alternatively, the control rod 330 may be coupled to the handle in a manner that limits the range of motion of the control rod 330 within the lumen of the cannula 304. For example, the lumen of the cannula 304 may include one or more stops which define the range of motion of the control rod 330 and thereby define the limits of blade rotation as the control rod 330 is adjusted.

From the open blade position shown in FIG. 9, the control rod 330 may be translated proximally within the lumen of the cannula 304. As the control rod 330 moves proximally, the distal angled surface 334 will be brought into contact with the blade heel 322. The angled distal surface 334 coincides with the angled blade heel 322 such that further proximal movement of the control rod 330 causes the blade 302 to pivot about the connection member 324 to bring the blade 308 down toward the retracted position shown in FIG. 8.

The illustrated embodiment shows angled surfaces 332 and 334 as substantially smooth surfaces. In other embodiments, one or more of the angled surfaces 332 and 334 may include grooves, teeth, or other structures configured to engage with corresponding structures disposed upon or attached to the blade 308.

Figure 10:
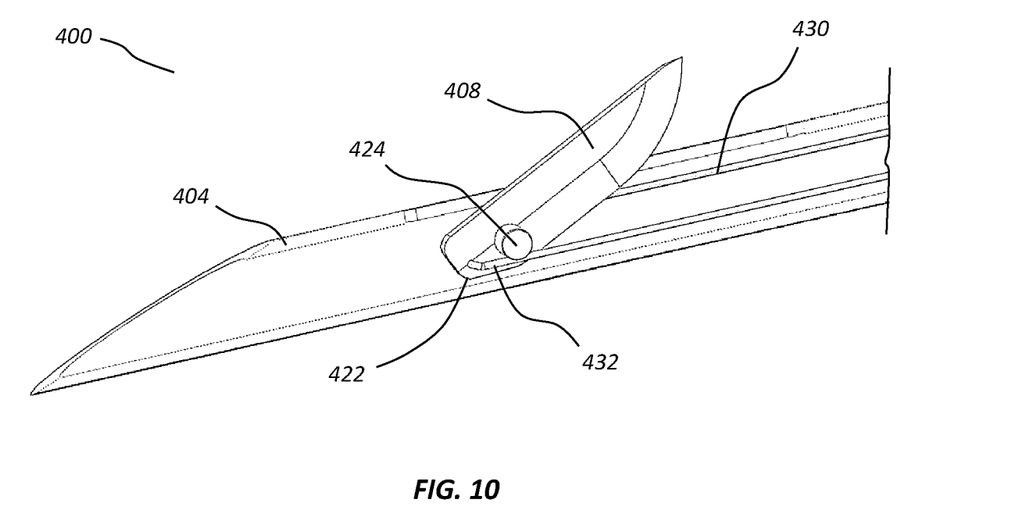
FIGS. 10 and 11 are left and right side cross-sectional views of a distal section of a subcutaneous cutting device showing an alternative control mechanism for opening and retracting the blade.
Figure 11:
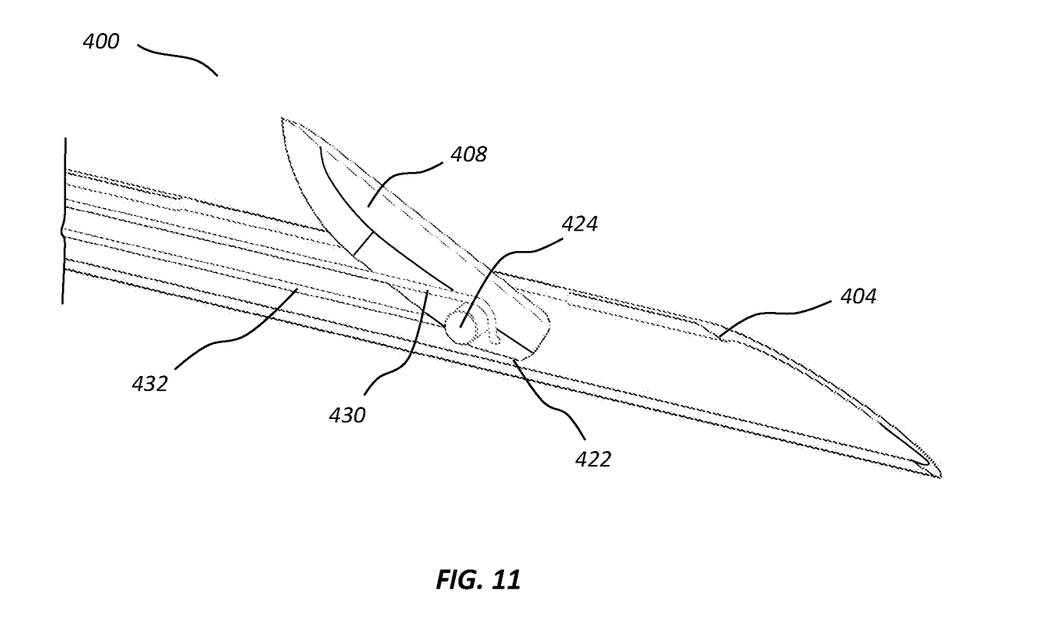

FIGS. 10 and 11 are cross-sectional views of another cutting device 400 showing an alternative control mechanism for adjusting the blade 408 between the retracted and open positions. FIG. 10 shows a left side cross-sectional view of the cutting device 400 and FIG. 11 shows a right side cross-sectional view of the device 400. As shown, a retracting control wire 430 and an opening control wire 432 are disposed within a lumen of the cannula 404. The control wires 430 and 432 are coupled to the blade 408 such that selective tensioning of the control wires 430 and 432 can control rotational position of the blade 408.

Although not shown in these views, the control wired 430 and 432 may extend proximally to a handle of the device, where one or more controllers of the handle may be manipulated by a device operator in order to selectively tension the retracting control wire 430 and/or opening control wire 432 (see handle 102 and controller 110 of FIG. 1).

As best shown in FIG. 10, the opening control wire 432 is disposed underneath the pivot point defined by the connection member 424. The opening control wire 432 is coupled to the blade 408 at a position relative to the pivot point such that when the opening control wire 432 is tensioned, the resulting forces cause the blade 408 to pivot about the connection member 424 and rotate toward the open position.

As with the embodiment shown in FIGS. 8 and 9, the blade 408 includes an angled blade heel 422 which limits over-rotation of the blade 408 and defines the full open position of the blade 408. Additionally, or alternatively, one or more of the control wires 430 and 432 may be coupled to the handle in a manner that limits range of motion within the lumen of the cannula 404 and thereby defines the extent of blade rotation.

As best shown in FIG. 11, the retracting control wire 430 is disposed over the pivot point defined by the connection member 424. The retracting control wire 430 is coupled to the blade 408 at a position relative to the pivot point such that when the retracting control wire 430 is tensioned, the resulting forces cause the blade 408 to pivot about the connection member 424 and rotate downwards toward the retracted position.

In the illustrated embodiment, the retracting control wire 430 and the opening control wire 432 are disposed on opposite sides of the blade 408. In other embodiments, the retracting control wire 430 and the opening control wire 432 may be disposed on the same side of the blade 408.

Cutting devices described herein may be formed from a variety of suitable medical-grade materials. For example, the cannula, blade, connection member, and/or other components may be formed from stainless steel. Alternatively, one or more components may be formed from other metals, alloys, or polymers suitable for medical-grade use. In some embodiments, one or more control wires are formed from a nickel-titanium alloy or other material with superelastic properties.

In some embodiments, a cutting device may include one or more radiopaque markers to aid in visualization an imaging during a procedure. For example, one or more radiopaque markers may be positioned on the blade, distal tip of the cannula, or other locations near the blade. In some embodiments, the blade may be micro-etched on one or both sides to denote where the blade will retract.

Ultrasound may be utilized in conjunction with a cutting device to provide visualization of the cutting device and/or the subcutaneous targeted tissue area. Such real-time monitoring allows the positional relationship between the cutting device and surrounding anatomical structures (such as nerves, arteries, veins, muscles, tendons, ligaments, and bones) to be monitored during a cutting procedure. In use, the cutting device may be positioned adjacent the targeted tissue, and a device operator may verify appropriate placement via ultrasound.

In some embodiments, a blade may be biased toward a default position. For example, the blade may be coupled to a spring configured to bias the blade toward the default position. In some embodiments, the blade may be biased toward the retracted position, and the biasing force may be overcome by appropriately adjusting the blade toward the open position (e.g., by moving a control rod or tensioning a control wire, as described by the foregoing). The blade may then remain in the open position for as long as the opening force is maintained. When the opening force is removed, the blade can automatically revert back into the default retracted position. Alternatively, the blade may be configured to be biased toward the open position. For example, the blade may be configured to "pop" open once the control mechanism (e.g., pull wire(s) or control rod) maintaining the retracted position is unlocked.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any of the blades described herein may be utilized with any of the control mechanisms described herein, and any element or component described in relation to a particular embodiment may be combined with or substituted for like components described in other embodiments.

The invention claimed is:

1. A medical device configured for cutting subcutaneous tissues, the medical device comprising:
   a handle disposed at a proximal end of the device;
   a cannula coupled to the handle and extending distally from the handle, the cannula including a distal tip and a blade-holding section near the distal tip;
   a blade disposed within the blade-holding section of the cannula, the blade including a tip, a spine, a heel, and a cutting edge, the blade being coupled to the cannula so as to be adjustable between a retracted position in which the blade is disposed within the blade-holding section of the cannula and an open position in which the blade tip is rotated away from the cannula, the blade tip being angled toward the handle when in the open position,
      wherein blade thickness tapers from the blade spine to the blade cutting edge, and
      wherein, when the blade is in the open position, the blade spine faces distally and the blade cutting edge faces proximally such that the device is configured for one-way, reverse movement during cutting of tissue; and
   a control mechanism operatively coupling the handle to the blade to enable selective adjustment of the blade between the retracted and open positions,
      wherein the control mechanism includes a control rod disposed within a lumen of the cannula and configured to be translatable within the lumen of the cannula, the control rod including one or more surfaces configured to engage with the blade to move the blade between the retracted and open positions as the control rod is moved within the lumen of the cannula, and
      wherein the control rod includes a proximal angled surface, the proximal angled surface being configured to engage with and lift the blade cutting edge as the control rod is moved distally to thereby lift and rotate the blade away from the cannula and toward the open position.

2. The device of claim 1, wherein the blade-holding section further includes a slot oriented along a longitudinal axis of the cannula, the slot being configured to provide passage of the blade tip out of and into the cannula when moved between the retracted and open positions.

3. The device of claim 2, wherein the blade spine is sized to substantially fill the slot when the blade is in the retracted position.

4. The device of claim 1, wherein the blade, when in the retracted position, is oriented such that the blade spine is substantially flush with an outer surface of the cannula.

5. The device of claim 1, wherein the blade, when in the open position, is oriented such that the blade spine faces away from the cannula and the blade cutting edge faces toward the cannula.

6. The device of claims 1, wherein the blade, when in the open position, is angled away from the cannula by an angle of about 10 degrees to about 60 degrees.

7. The device of claim 1, wherein the blade, when in the open position, is angled away from the cannula by an angle of about 15 degrees to about 45 degrees.

8. The device of claim 1, wherein the distal tip of the cannula is sharpened.

9. The device of claim 1, wherein the handle includes a controller operatively coupled to the control mechanism such that manipulation of the controller manipulates the control mechanism to thereby adjust a position of the blade.

10. The device of claim 1, wherein the blade is pivotally coupled to the cannula by a connection member disposed near the blade heel, the connection member thereby enabling the blade tip to rotate away from the cannula when moved toward the open position.

11. The device of claim 10, wherein the connection member is stationary relative to the cannula as the blade is moved between the open and retracted positions.

12. The device of claim 1, wherein the blade heel includes an angled backstop configured to contact an inner surface of the cannula to limit further rotation of the blade.

13. A medical device configured for cutting subcutaneous tissues, the medical device comprising:
   a handle disposed at a proximal end of the device;
   a cannula coupled to the handle and extending distally from the handle, the cannula including a sharpened distal tip and a blade-holding section near the distal tip;
   a blade disposed within the blade-holding section of the cannula, the blade including a tip, a spine, a heel, and a cutting edge, the blade being coupled to the cannula so as to be adjustable between a retracted position in which the blade is disposed within the blade-holding section of the cannula and an open position in which the blade tip is rotated away from the cannula; and
   a control rod operatively coupling the handle to the blade to enable selective adjustment of the blade between the retracted and open positions, the control rod comprising one or both of
      a proximal angled surface configured to engage with and lift the blade cutting edge as the control rod is moved distally to thereby lift and rotate the blade away from the cannula and toward the open position, or
      a distal angled surface positioned so as to not contact the blade heel when the blade is in the open position and being configured to engage with the blade heel when the control rod is moved proximally to thereby rotate the blade toward the cannula and toward the retracted position.

14. The device of claim 13, wherein the blade tip is angled toward the handle when in the open position.

15. The device of claim 13, wherein the blade heel includes an angled backstop configured to contact an inner surface of the cannula to limit further rotation of the blade.

16. A medical device configured for cutting subcutaneous tissues, the medical device comprising:
   a handle disposed at a proximal end of the device;
   a cannula coupled to the handle and extending distally from the handle, the cannula including a distal tip and a blade-holding section near the distal tip;
   a blade disposed within the blade-holding section of the cannula, the blade including a tip, a spine, a heel, and a cutting edge, the blade being coupled to the cannula so as to be adjustable between a retracted position in which the blade is disposed within the blade-holding section of the cannula and an open position in which the blade tip is rotated away from the cannula, the blade tip being angled toward the handle when in the open position,
   wherein blade thickness tapers from the blade spine to the blade cutting edge, and
   wherein, when the blade is in the open position, the blade spine faces distally and the blade cutting edge faces proximally such that the device is configured for one-way, reverse movement during cutting of tissue; and
   a control mechanism operatively coupling the handle to the blade to enable selective adjustment of the blade between the retracted and open positions,
   wherein the control mechanism includes a control rod disposed within a lumen of the cannula and configured to be translatable within the lumen of the cannula, the control rod including one or more surfaces configured to engage with the blade to move the blade between the retracted and open positions as the control rod is moved within the lumen of the cannula, and
   wherein the control rod includes a distal angled surface, the distal angled surface positioned so as to not contact the blade heel when the blade is in the open position and being configured to engage with the blade heel when the control rod is moved proximally to thereby rotate the blade toward the cannula and toward the retracted position.

17. The device of claim 16, wherein the blade, when in the retracted position, is oriented such that the blade spine is substantially flush with an outer surface of the cannula.

18. The device of claim 16, wherein the blade, when in the open position, is oriented such that the blade spine faces away from the cannula and the blade cutting edge faces toward the cannula.

19. The device of claims 16, wherein the blade, when in the open position, is angled away from the cannula by an angle of about 10 degrees to about 60 degrees.

20. The device of claim 16, wherein the distal tip of the cannula is sharpened.

* * * * *